(12) United States Patent
Nitzan et al.

(10) Patent No.: US 7,756,579 B2
(45) Date of Patent: Jul. 13, 2010

(54) IMPLANTABLE SENSOR

(75) Inventors: Yaacov Nitzan, Tel-Aviv (IL); Ben-Zion Spector, Haifa (IL)

(73) Assignee: Depuy International Ltd., Leeds (GB)

( * ) Notice: Subject to any disclaimer, the term of this patent is extended or adjusted under 35 U.S.C. 154(b) by 183 days.

(21) Appl. No.: 11/063,160

(22) Filed: Feb. 22, 2005

(65) Prior Publication Data

US 2006/0189898 A1 Aug. 24, 2006

(51) Int. Cl.
*A61N 1/00* (2006.01)
(52) U.S. Cl. .......................................... 607/19
(58) Field of Classification Search ................ 607/19; 600/561, 587; 604/9; 623/17.12
See application file for complete search history.

(56) References Cited

U.S. PATENT DOCUMENTS

| | | | |
|---|---|---|---|
| 3,111,125 A * | 11/1963 | Schulte | 604/9 |
| 3,958,558 A | 5/1976 | Dunphy et al. | |
| 3,958,562 A * | 5/1976 | Hakim et al. | 600/561 |
| 4,494,411 A | 1/1985 | Koschke et al. | |
| 5,083,573 A * | 1/1992 | Arms | 600/587 |
| 5,089,004 A | 2/1992 | Averill et al. | |
| 5,171,270 A * | 12/1992 | Herrick | 623/11.11 |
| 5,231,996 A | 8/1993 | Bardy | |
| 5,246,014 A | 9/1993 | Williams | |
| 5,584,873 A | 12/1996 | Shoberg | |
| 5,755,743 A | 5/1998 | Volz et al. | |
| 5,760,341 A | 6/1998 | Laske | |
| 6,053,873 A * | 4/2000 | Govari et al. | 600/505 |
| 6,132,384 A | 10/2000 | Christopherson et al. | |
| 6,198,969 B1 | 3/2001 | Kuzma | |
| 6,572,543 B1 | 6/2003 | Christopherson | |
| 6,801,809 B2 | 10/2004 | Laske | |
| 2003/0078671 A1 | 4/2003 | Lesniak et al. | |
| 2004/0034355 A1 | 2/2004 | Govari | |
| 2004/0068260 A1 | 4/2004 | Cossette et al. | |
| 2004/0186576 A1 * | 9/2004 | Biscup et al. | 623/17.12 |

FOREIGN PATENT DOCUMENTS

| | | |
|---|---|---|
| EP | 1321097 A2 | 6/2003 |
| WO | WO 01/56513 A1 | 8/2001 |
| WO | WO 03/073959 A2 | 9/2003 |
| WO | WO 2005/000090 A2 | 1/2005 |

OTHER PUBLICATIONS

PCT Search Report, Aug. 31, 2006, 30 pages.
GB Search Report dated May 19, 2005, 1 page.

* cited by examiner

*Primary Examiner*—George Manuel

(57) ABSTRACT

A sensor which can be implanted in a body part to collect data relating to the body part, the sensor includes a jacket which has a side wall which can be deformed inwardly, and first and second ends. A sensor part is contained within the jacket, and fastened to the jacket at or towards the first end of the jacket. The sensor part is at least partially isolated from compressive forces applied to the sensor which cause the side wall of the jacket to deform inwardly.

20 Claims, 3 Drawing Sheets

IMPLANTABLE SENSOR

BACKGROUND TO THE INVENTION

The present invention relates to an implantable sensor and in particular to a sensor which can be implanted in a bone to be tracked by a tracking system.

Sensors which can be implanted into a body part of a patient can be used in surgical procedures for many applications. For example, implantable sensors can be used for measuring the temperature of a body part in which the sensor is located, and for measuring the amount of stress a body part is under. In particular, a sensor can be used to provide a registration mark whose location can be determined and tracked by a tracking system. Such a sensor can be implanted in a body part, such as a bone, so that the position of the bone can be tracked, e.g. during a surgical procedure.

When the sensor is used as a marker, a system in which the sensor is incorporated can be used to track the location of the sensor. This can be achieved using electromagnetic techniques. U.S. Pat. Nos. 5,391,199 and 5,443,489 provides details of systems which are applicable to the present invention, in which the coordinates of an intrabody probe are determined using one or more field transducers, such as a Hall effect device, coils, or other antennae carried on the probe. Such systems are used for generating location information regarding a medical probe or catheter. A sensor, such as a coil, is placed in the probe and generates signals in response to externally-applied magnetic fields. The magnetic fields are generated by magnetic field transducers, such as radiator coils, fixed to an external reference frame in known, mutually-spaced locations. Systems which are concerned with tracking a sensor in a three-dimensional space are also disclosed in WO-96/05768, U.S. Pat. No. 6,690,963 and US-A-2002/0065455. Subject matter that is disclosed in the specifications of the patents and patent applications referred to in this paragraph is incorporated in this specification for all purposes by these references.

Implantable sensors are typically implanted immediately prior to a surgical procedure and can subsequently be removed immediately after the completion of the procedure. An implantable sensor of this kind can have a threaded exterior surface, allowing the sensor to be implanted in the bone with a screwing action, and removed from the bone by the reverse unscrewing action.

It is important that such a sensor is securely held within the body part so as to prevent movement of the sensor once it has been implanted. Any movement of the sensor within the body part can be undesirable, especially when the sensor is used for tracking purposes, because any such movement can lead to inaccuracies in the tracking of the sensor and the body part in which it is implanted. Further, in order to minimise the duration of the medical procedure by which the sensor is implanted, it can be desirable that the sensor can be easily implanted and removed from its site in the body part.

SUMMARY OF THE INVENTION

The present invention provides an implantable sensor in which the sensor part is enclosed by jacket which can be deformed inwardly.

Accordingly, in a first aspect, the invention provides a sensor which can be implanted in a body part to collect data relating to the body part, the sensor comprising: a jacket which has a side wall which can be deformed inwardly and first and second ends, a sensor part which is contained within the jacket and is fastened to the jacket at or towards the first end of the jacket, so that the sensor part is at least partially isolated from compressive forces applied to the sensor which cause the side wall of the jacket to deform inwardly.

The sensor of the invention has the advantage that the ease by which the implantable sensor can be implanted into the bone is significantly increased over existing implantable sensors. The use of a jacket that can be deformed inwardly allows the implantable sensor to be pushed into a previously prepared hole in the bone. This removes the need to apply a torsional force to the sensor during its implantation. This can be particularly advantageous as it can be difficult to impart a rotational force on implantable sensor, particularly because implantable sensors usually have very small dimensions. Further, an implantable sensor can have a cord extending from one of its ends, for example, to facilitate extraction of the implantable sensor. During implantation of an existing implantable sensor, the cord can become twisted. The present invention removes the need to rotate the sensor and therefore avoids twisting of the cable which can damage the sensor or cord or both.

When an implantable sensor according to the present invention is implanted in the bone, the jacket is compressed within the hole. The elastic property of the jacket urges the jacket against the inner walls of the hole, and as a result the implantable sensor is held tight within the hole. Current implantable sensors can become loose from their site in the body part. For example, when the sensor is to be implanted in a bone, the anchorage of the sensor in the bone can be reliant on the thread of the screw thread cutting into the bone. If the bone is brittle, then it can be difficult to obtain a clean cut into the bone and therefore it can be difficult to securely anchor the sensor within the bone. As the present invention relies on compression forces rather than cutting forces, the implantable sensor of the present invention is not as affected by such problems. Accordingly, the use of a jacket that can deform inwardly can decrease the risk of the implantable sensor moving inadvertently relative to the bone during the medical procedure.

The use of deformable jacket to engage the wall of a hole in a body part such as a bone can help to avoid problems of insecure fixation due to inaccuracies in the preparation of the hole. For example, a hole might be made slightly bigger than is desirable for secure fixation. In the case of a sensor which engages the hole wall by means of a screw thread, the connection that is provided by the screw thread can be less secure than intended. The resilient nature of the jacket of the sensor of the invention can facilitate secure fixation, accommodating variations in the shape and dimensions of the hole.

Furthermore, it has been found that the use of a jacket that can deform inwardly can increase the ease by which the implantable sensor can be removed from the bone. Implantable sensors that utilise a screw thread require a rotational force to be imparted on the implantable sensor which as described above can be difficult. The sensor of the present invention, can be removed by pulling the sensor out of the hole, along its axis. Little or no rotational force need be imparted on the sensor of the present invention in order to remove it.

When the sensor according to the present invention has a cord extending from one of its ends, the sensor can be removed by pulling on the cord attached to the end of the sensor with a sufficient force along the axis of the sensor. The use of a jacket can therefore enable the implantable sensor to be removed without the use of a third party instrument. This can greatly simplify the removal of the sensor as the surgeon does not need to locate a third party instrument on the sensor in order to do so. This can be particularly difficult when the dimensions of the sensor are very small.

It has also been found that the use of a jacket that can deform inwardly can decrease the dimensions of the implantable sensor. This is particularly true when the sensor includes a cord as no provision need be made on the implantable sensor which allows it to be attached to a third party implement in order to impart a rotational force on it. This can enable the implantable sensor to be designed so as to be more compact.

The cross-sectional shape of the sensor along its length will generally be uniform. The cross-sectional shape of the sensor will generally be circular. It will be understood that the cross-sectional shape can be any other regular or irregular shape, for example square or triangular.

The cross-sectional size of the sensor will be generally uniform along at least part of its length. However, it can be preferable for the cross-sectional size to decrease towards its ends. This can aid insertion and removal of the sensor from the body part. For example, the ends of the sensor can be tapered towards a point. For example, when the cross-sectional shape of the sensor is generally circular, the end sections of the sensor can be generally conical. A taper at one end of the sensor can also allow attachment of a cord without affecting the ability of the sensor to fit into a hole in the bone or other body part.

Preferably, the cross-sectional shape of the jacket along at least part of its length is circular. The cross-sectional shape of the jacket will generally be the same as that of the sensor part. For example, when the cross-sectional shape of the sensor part is circular, the cross-sectional shape of the jacket can also be circular. However, it will be appreciated that this need not be the case and the jacket and sensor can have different cross-sectional shapes.

Preferably, the jacket has at least one compression line that extends generally between the first and second ends which facilitates inward deformation of the jacket. A compression line can be any formation in the jacket which extends along the length of the jacket which facilitates inward deformation of the jacket. The provision of at least one compression line can help ensure that the jacket is able to compress sufficiently for it to be fitted within a prepared hole in a bone or other body part. It can also ensure that the jacket compresses in a controlled manner. It has been found that the provision of a compression line can allow the inward deformation of the jacket (with any associated creasing) to be controlled and as a result can help prevent the jacket from creasing undesirably. The proper deformation of the jacket can help to make the anchorage of the sensor within the bone more secure. It can also increase the reusability of the sensor.

Preferably, the compression line extends along at least 60% of the length of the jacket, more preferably at least 70% of the length of the jacket, especially preferably at least 80% of the length of the jacket, for example at least 90% of the length of the jacket. The greater the proportion of jacket along which the compression line extends, the greater proportion of the jacket that facilitates inward deformation.

Preferably, the jacket has at least two compression lines spaced around the jacket. The provision of two compression lines can increase the amount by which the jacket can be inwardly deformed. More preferably, the jacket has at least three compression lines, especially preferably at least four compression lines. Preferably the compression lines are spaced apart around the jacket approximately equally. This can help to ensure that the jacket deforms evenly.

As will be understood, a compression line can reduce the structural integrity of the jacket. Preferably, the jacket has not more than eight compression lines. More preferably the jacket has not more than six compression lines, especially preferably not more than five compression lines.

The compression line can be a longitudinally extending crease which facilitates folding of the jacket along the crease. The use of a crease can be advantageous as the crease can be formed so that when the jacket folds along the crease, the jacket along the fold protrudes radially outward relative to the sensor. This can increase the amount by which the jacket is compressed in the hole, and therefore can increase the force by which the jacket is urged against the walls of the hole in which the sensor is implanted. Therefore, the use of a crease can increase anchorage of the sensor in the body part.

Preferably the compression line is in the form of a longitudinally extending slit formed in the jacket. This can be advantageous as it can allow the jacket to deform inwardly without restriction. Also, as the jacket is urged radially outward once compressed in a hole, the edges of the slits can tend to catch against the walls of the hole. This has been found to enhance the stability and anchorage of the sensor in the hole. Furthermore, a jacket in which the compression line is a slit can also be manufactured easily by simply cutting a section of the jacket.

Preferably, the jacket and slit are configured so that when the sensor is implanted in the body part, the opposing longitudinal edges of the slit come close to abutting.

The greater the width of the slit between its opposing longitudinal edges, the greater the inward deformation of the jacket facilitated by the slit. Preferably, the ratio of the circumference of the jacket to the width of the slit is not more than about 10, more preferably not more than about 5, especially preferably no more than about 2. Preferably, the width of the slit, between opposing longitudinal edges, is at least about 0.1 mm, more preferably at least about 0.2 mm.

The greater the width of the slit between its opposing longitudinal edges, the greater the reduction in structural integrity. Also, the greater the width of the slit between its opposing longitudinal edges, the more easily the jacket will compress, therefore the less the jacket will resist being compressed, and hence the smaller the retaining force provided by the jacket. Preferably, the width of the slit is not more than about 2.0 mm, more preferably not more than about 1.0 mm, especially preferably no more than about 0.4 mm.

Preferably, the proportion of the of the jacket that is open in a band that extends around the circumference of the jacket and which is arranged such that its plane is perpendicular to the axis of the jacket, is not more than 50%, more preferably not more than 25%, especially preferably no more than 10%.

There can be a cord connected to the sensor. The cord can be a signal carrying wire which can be connected to, and facilitate communication between, the sensor part and an external device. The cord can carry power to the sensor where this is required in order for the sensor to produce a signal.

A wire which extends from the sensor can carry a signal from teh sensor to an external component. For example, the signal can be carried to a system controller, in particular which is able to analyse the signal. The wire can extend from teh sensor to an external pad which can be fastened to teh patient's skin or to another convenient surface, for example on the operating table. Preferably, the sensor generates a field when it moves within a magnetic field which is generated by a local magnetic field generator provided on a pad which is adapted to be affixed to a surface of the body of the patient. The pad can include a plurality of concentric orthogonal magnetic field generating coils. A driving antenna can be provided to radiate a radio frequency (RF) electromagnetic field. The pad can include a power coil which is coupled to receive the RF electromagnetic field and thereby to provide power for generating the magnetic field. Alternatively, the pad can include an internal power source to provide power for generating the magnetic field. It can however be particularly preferred for the pad to be connected by means of conductors to a source of electrical power.

A local magnetic field generator which is provided on a pad can be used in conjunction with a position sensor which is implanted in a patient's body, to provide information about the patient, in particular as to the location and orientation of the part of the body in which the sensor is implanted.

Tracking systems which comprise a pad on which a magnetic field can be generated and at least one position transducer are disclosed in a US patent application which is filed with the present application, entitled Reference Pad for Position Sensing. Subject matter that is disclosed in the specification of that patent application is incorporated in this specification for all purposes by these references.

Preferably, the sensor includes a cord which is connected to the jacket, by which force can be applied to the sensor to remove it from the body. The cord can include a signal carrying wire which can be connected to, and facilitate communication between, the sensor part and an external device.

Preferably, the cord comprises a load bearing core for transferring force to the jacket, and at least one signal carrying wire for carrying electronic signals to and/or from the sensor part. It can be preferable to provide a load bearing core in order to help prevent any load being borne by the signal carrying wire, in particular during extraction of the sensor. This is because, the signal carrying wire, and/or the connection between the signal carrying wire and the sensor part, can be structurally weak and not able to withstand forces required to extract the sensor from the body part.

Preferably, the sensor includes a force transfer member to which the cord is connected. Preferably, the force transfer member is a bar that extends across the jacket between opposite side walls, and in which the cord is connected to the bar. Preferably, it is the core of the cord that is attached to the bar, for example by means of a knot or of a crimped ferrule.

The core of the cord can be made of any material which can withstand forces exerted upon the core during removal of the sensor in the body part. For example, preferably the core can withstand forces of at least 10 kg, more preferably at least 15 kg, especially preferably at least 20 kg, for example 25 kg. The core can be made of fishing wire. The core can be made of extruded polyethylene wire. The core can be made of an aramid fibre.

Preferably, the signal carrying wire is a twisted pair of insulated copper wire. Preferably, the signal carrying wire is coated in an insulating material. For example, the signal carrying wire can be coated with a low friction polymer such as a polytetrafluoroethylene.

Preferably, there are at least two signal carrying wires, more preferably at least three signal carrying wires.

Preferably, the cord includes an insulating member so as to shield the sensor carrying wire from electrical noise created by external devices. Preferably, the insulating member is an inner coating formed on the inside of the cord.

Preferably, the sensor is connected to the force transfer member.

Preferably, the connection between the sensor part and the force transfer member is embedded in a body of a resin material. Preferably, the connection between the sensor part and the bar is encapsulated by a resin material. Preferably, the sensor part and the bar are encapsulated by a resin material. Preferably, the jacket encloses the resin material. It can be preferable to encapsulate the sensor part within an resin material as this can help prevent the ingress of moisture during use of the sensor. It can also help to provide some structural rigidity and stability to the sensor part. This can be useful when the sensor part contains delicate electronics. Preferably, the resin material is an epoxy resin. Preferably, the resin material is moulded around the sensor part and the bar.

Preferably, the bar is in the form of a generally cylindrical bar extending between opposing sides of the jacket. Preferably, the length of the bar is greater than the width of the sensor part so as to allow the jacket to be attached to the ends of the bar. Preferably, the bar is made of a sufficiently strong and rigid material so as to withstand forces exerted upon it by the cable during removal of the sensor. The connection between the sensor part and the bar should be sufficiently strong so as to withstand compression and tension forces exerted on the bar during insertion and removal of the sensor. When the sensor part and the bar are encapsulated by a mould of epoxy resin, this can increase the strength of the connection between the bar and the sensor part.

As will be understood, the sensor need not necessarily include a cord to allow the sensor part to be connected to, and to facilitate communication with, an external device. The sensor can include a wireless transmitter, receiver or transceiver for sending and/or receiving signals to an external device. Further, the sensor need not necessarily send signals to an external device during the medical procedure. For example, the sensor could include memory which can store data which can be transferred to an external device subsequent to the medical procedure.

Preferably, the jacket is tapered inwardly at at least one of the first and second ends. This can aid implantation and extraction of the sensor. In particular, when the end of the jacket which is to be inserted into the hole first is tapered, this can increase the ease by which the sensor can be located in the hole and hence implanted into the body part.

Preferably, the jacket comprises a first portion at the first end, a second portion at the second end, and a third portion between the first and second ends. The provision of different portions can allow the different portions to have different characteristics. For example, preferably the first and second portions are tapered towards their free ends, and the width and shape of the third portion is substantially uniform along at least part, preferably all, of its length.

This is particularly true when the width of the third portion is significantly greater than the width of the sensor part which it encapsulates. This is because the jacket can be compressed and deform to allow the sensor to be implanted into a hole which has a width less than the width of the jacket, but greater than the sensor. Preferably, the average transverse dimension (which will be the diameter when the jacket has a circular cross-section) of the third portion is at least 5% greater than the width of the sensor part which is surrounded by the third portion, more preferably at least 10%, especially preferably at least 20%, for example, at least 40%.

Preferably, the width of the third portion is substantially uniform along its length. Preferably, the cross-sectional shape of the jacket along taken in a direction perpendicular to the axis of the third portion is approximately constant along its length. Therefore, when the cross sectional shape of the jacket is generally circular, the third portion is generally cylindrical.

Preferably, the ratio of the length of the third portion (measured along the jacket) to the length of the first portion is at least about two, more preferably at least about three, especially preferably at least about four, for example at least about five. Preferably, the ratio of the length for the third portion to the length of the second portion is at least about two, more preferably at least three, especially preferably at least four, for example five. Therefore, the length of the third portion is preferably longer than the length of the first and second portions. This is especially preferable when the first and second portions taper inwardly as towards the ends of jacket, because it will generally be the third portion that provides a significant proportion of the retaining force which helps to hold the sensor in place in the body part.

Preferably, the compression line extends along the entire length of the third portion. Preferably, the compression line extends into the first portion. Preferably, the compression line extends into the second portion.

Preferably, the compression line extends along at least 25% of the length of the first portion (measured in a direction parallel to the axis of the first portion), more preferably at least 35%, especially preferably at least 40%, for example at least 45%. Preferably, the compression line extends along not more than 90% of the length of the first portion, more preferably not more than 70%, especially preferably not more than 60%, for example not more than 50%.

Preferably, the compression line extends along at least 25% of the length of the second portion taken in a direction parallel to the axis of the second portion, more preferably at least 35%, especially preferably at least 40%, for example at least 45%. Preferably, the compression line extends along not more than 90% of the length of the second portion, more preferably not more than 70%, especially preferably not more than 60%, for example not more than 50%.

The three portions of the jacket can be formed from separate pieces of material, joined together at their ends. Preferably, the three portions of jacket are formed from material having the same material properties. More preferably, the three portions of the jacket are formed from separate pieces of the same material.

It is however particularly preferred that the jacket is formed from a single piece of material, for example from a sheet of material that is welded or otherwise bonded along a seam, or by an extrusion technique, possibly in combination with cutting and bonding steps. This can be simpler to manufacture than a jacket which is formed in three portions joined together at their ends.

Preferably, the side wall of the jacket is sufficiently resilient so that it returns substantially back to its original shape upon removable of an external force after it has been deformed. Preferably, the side wall of the jacket is sufficiently resilient so that once it has been deformed by placing the sensor in a hole in a body part, the jacket is urged against the inner walls of the hole so as to provide a retaining force which is sufficient to hold the sensor in place. Preferably, the side wall of the jacket is sufficiently resilient so that, when the sensor is implanted in a hole in a bone, a force of at least 3 kg in an outward direction parallel to the axis of the sensor is required to pull the sensor out of the bone, more preferably at least 4 kgf, especially preferably at least 5 kgf. Preferably, the force required to pull the sensor out of the bone is less than 8 kgf, more preferably less than 7 kgf, especially preferably less than 5 kgf.

The material of the jacket may deform plastically on insertion into the hole in the body part.

A jacket can be made of any material having the aforesaid properties. A jacket can be made from a metallic material (including an alloy) having the aforesaid properties. For example, the jacket could be made from a shape-memory alloy, stainless steel or titanium. A jacket can be made from a polymeric material having the aforesaid properties.

In another aspect, the invention provides a method of making a sensor which can be implanted in a body part to provide data to a computing system, the method comprising: attaching a sensor part to a first end of a jacket which has a side wall that can be deformed inwardly so that the sensor part is contained within the jacket and at least partially isolated from compressive forces applied to the sensor which cause the side wall of the jacket to deform inwardly.

Preferably, the method includes the step of encapsulating the sensor part and force transfer member in an epoxy resin before the step of attaching the jacket.

The sensor of the invention can be implanted using an instrument which comprises:

a guide sheath for defining a path to the surface of the body part through overlaying soft tissue, the sheath having a bore extending along its length between first and second open ends through which the tool can pass and a slot that extends along its length between its first and second open ends; and a delivery sheath for inserting the sensor in the hole, the delivery sheath having a bore extending along its length between a first open end at which the sensor can be mounted and a second end, with the wire extending from the sensor along the bore, in which the sheath has a slot that extends along its length between its first and second end, and wherein the delivery sheath can be received within the guide sheath by sliding the delivery sheath within the bore of the guide sheath;

wherein the slots of the guide and delivery sheaths can be aligned to allow the wire to be removed from the bores other than at the ends of the bores.

Such an instrument is disclosed in the European and US patent applications filed with the present application with the title An Instrument for Implanting a Sensor. Subject matter that is disclosed in the specification of that application is incorporated in this specification for all purposes by this reference.

INTRODUCTION TO THE DRAWINGS

DESCRIPTION OF PREFERRED EMBODIMENTS

Figure 3:
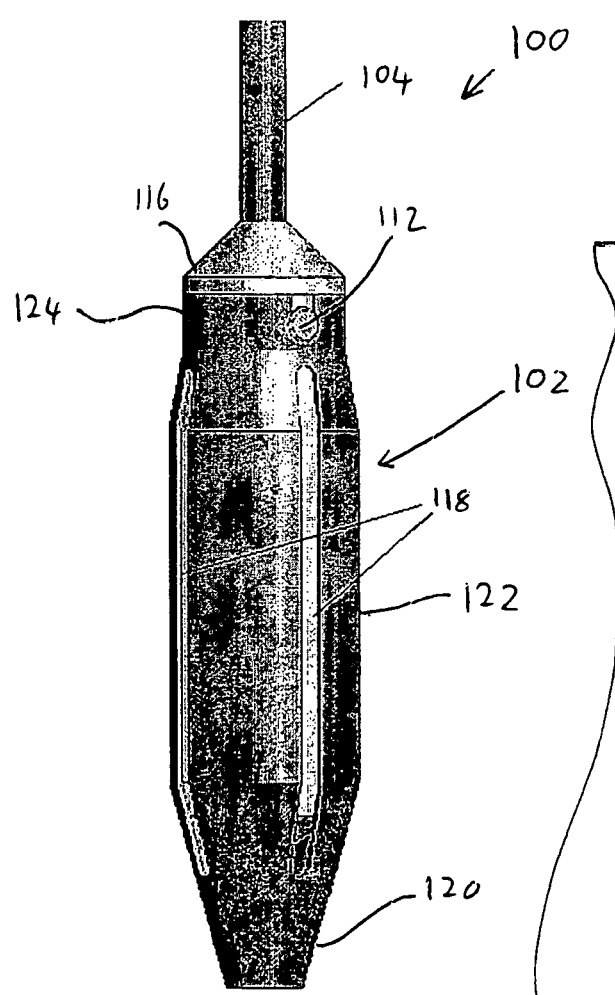
FIG. 3 shows a schematic illustration of the sensor shown in FIG. 1.

Referring to the drawings, FIG. 3 shows a schematic illustration of an implantable sensor 100 according to the invention. For illustrative purposes only, the sensor described hereinafter is a sensor that can be tracked by a tracking system in order to track the location of the body part in which the sensor is implanted. Also as described hereinafter, the sensor is implanted in a bone. However, as will be understood and as described above, the invention can be used with other sensors used for different purposes, and that can be implanted into body parts other than a bone.

Figure 1:
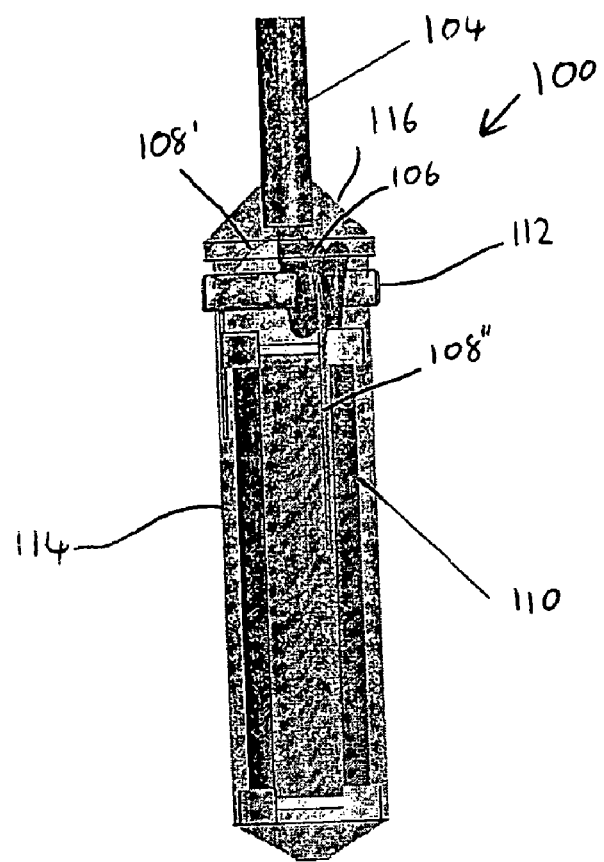
FIG. 1 shows a schematic longitudinal cross section through a sensor according to the invention.

The sensor includes an external jacket 102 which encloses a sensor part 110, as illustrated in FIG. 1. FIG. 1 shows a view of the sensor 100 with external jacket 102 removed. Sensor part 110 includes a body or bobbin around which three mutually perpendicular coils of 10 μm diameter wire are wound. In use, the three mutually perpendicular coils generate electrical signals via induction owing to the location of the sensor part in a time varying magnetic field. The signals generated by the coils are proportional to the strength of three perpendicular components of the magnetic field, from which the position of the sensor part in the magnetic field and the orientation of the sensor part can be determined. The two ends of each coil are soldered to a contact pad toward the distal or free end of the sensor. The sensor part may be a Hall effect device, coils, or other antennae which can be contained in the shaft. A example of a suitable coil sensor part is disclosed in US-A-2003/0120150 (Govari). The disclosed sensor part includes at least one sensing coil which can generate a signal when it moves within an electromagnetic field transmitted by a local transmitter. The disclosed coil sensor part is able to provide position information in multiple degrees of freedom, including up to six degrees of freedom. It can be preferred for the probe of the present invention to provide position information in six degrees of freedom, although less detailed information can be appropriate for some applications, for example at least three degrees of freedom, preferably at least four degrees of freedom, more preferably at least five degrees of freedom.

Figure 2:
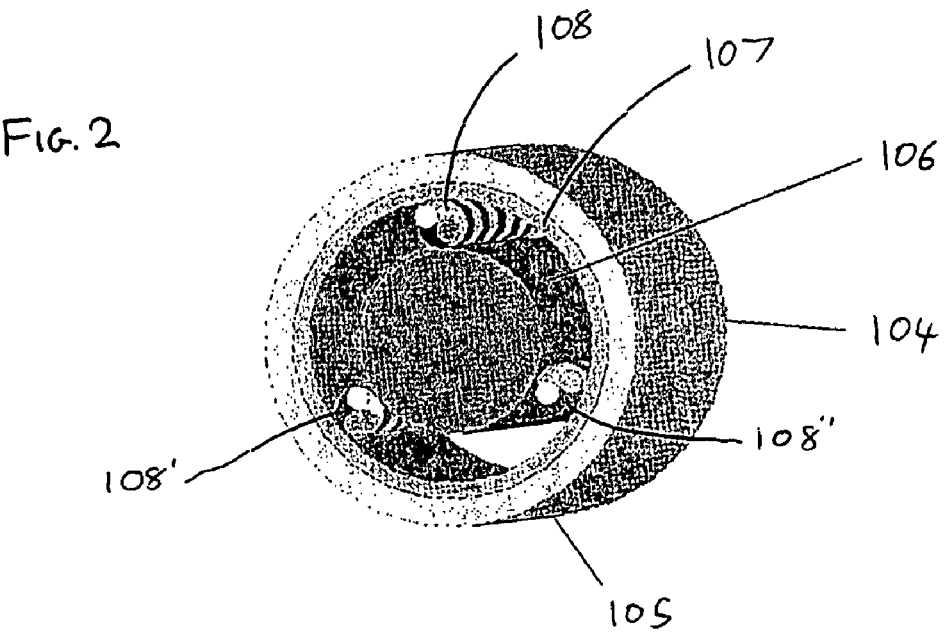
FIG. 2 shows a transverse cross section through a cable part of the sensor.

Sensor 100 also includes a cord 104. FIG. 2 shows a transverse cross section through cord 104. The cord 104 includes a central load bearing core 106 having a diameter of approximately 0.3 mm. The cord 104 has an outer diameter of approximately 2.8 mm. The core 106 can be made of any suitable material which can handle forces up to approximately 20 kg, such as an aramid fibre (especially that sold under the trade mark Kevlar), or extruded polyolefin (especially polyethylene) wire or fishing wire. Arranged around core 106 are three twisted pairs of insulated copper wire, each having a diameter of approximately 40 microns. The wire may be a low friction polymer such as a polytetrafluoroethylene (PTFE) (such as that sold under the trademark Teflon) coated or have some other insulating coating. Each twisted pair 108 carries an electrical signal from a respective one of the coils of the sensor part 110. The cord 104 also includes an inner coating 107 providing electrical insulation and also to shield electrical noise, such as white noise and electrical cross talk. Finally, an outer coating 105 is provided. The outer coating 105 can be of PTFE, polyethylene or any other similar bio-compatible material, and provides an interface between the cord and soft tissue of a patient in use.

Each wire of the twisted pair 108 of cord 104 is attached to respective contact pads for respective coils to provide electrical communication between the signals generated by the sensor coils and the cord.

The sensor also includes a circular bar 112 extending transversely across the sensor. The internal core 106 of cord 104 is tied around bar 112 using a hitch knot, or similar, non-slipping knot, so that loads on cord 104 are transferred to bar 112 which acts as a force transfer member.

The sensor part 110, bar 112 and cord 104 are held together by a moulded epoxy resin 114 which provides some structural rigidity to the sensor and encapsulates the sensor part and electronics so as to hermetically seal the sensor part and electronics. The epoxy resin material also acts to attach the sensor part to the bar 112 and also to stabilise the cord 104 toward the proximal end of the sensor. The epoxy resin toward the proximal end of the sensor has a shoulder structure 116.

Jacket 102 is made of a metal or alloy, such as 316 stainless steel or titanium. The jacket can be assembled from a piece of sheet metal bent into the appropriate profile and laser welded along a longitudinal seam. Alternatively, the jacket can be manufactured from three tubular sections which are joined together by circumferential laser welding. The jacket has a thickness of approximately 0.1 mm and has a plurality of gaps or cut outs 118 therein. The jacket has a tapered leading free end 120 which acts to automatically locate the free end of the sensor in a hole in use. A central body section 122 of the jacket has a diameter of approximately 2.8 mm and is slightly larger than the diameter of a hole into which the sensor is to be press fitted. An upper or neck portion 124 of the jacket has a diameter substantially matching that of the hole into which the sensor is to be press fitted and provides continuous smooth fit with the shoulder portion 116 of the epoxy resin encapsulate. The jacket 102 is attached to the remainder of the sensor by laser welding to the free ends of bar 112. Hence the jacket 102 encloses sensor part 110 and loads impinging on jacket 102 are transferred to force transfer member 112 rather than to the sensor part which is isolated from forces applied to the jacket.

Figure 4:
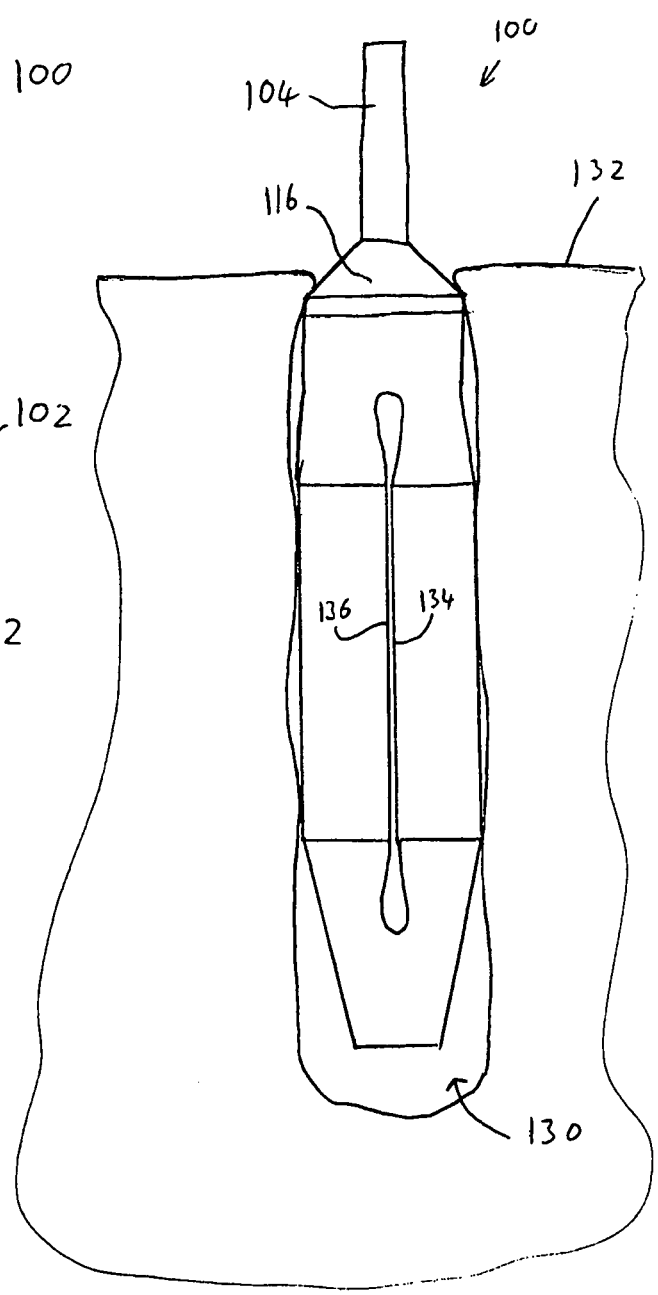
FIG. 4 shows a schematic illustration of the sensor shown in FIG. 1 located in a bone.

The body portion 122 of the jacket acts similarly to a leaf spring so that the jacket is resiliently deformable to secure locate the sensor in a patient's bone in use. FIG. 4 shows a schematic illustration of the sensor 100 located in use in a drilled hole 130 in a bone 132 of a patient. The hole 130 has been pre-drilled in the patient's bone using a drill having a drill bit with a diameter of approximately 2.6 or 2.7 mm. As illustrated in FIG. 4, a hole drilled in bone typically does not have a smooth well defined surface but rather the shape of the hole varies with depth. The sensor 100 is press fitted in hole 130. Initially the leading distal end 120 helps to guide the sensor into the aperture of hole 130. As the sensor is pushed into hole 130 the jacket deforms as the jacket has a diameter greater than that of the hole. As illustrated in FIG. 4, the slits 118 of the jacket are sized or otherwise configured such that when the jacket is fully deformed in the hole, the edges of the slits, 134, 136, abut, or come close to abutting, so as to close the slits. The slits are also required in order to allow the diameter of the jacket to reduce as the sensor is pushed into the hole 130. When the sensor is implanted in the hole, the elastic property of the material of the jacket urges the walls of the body of the jacket against the inner walls of the hole so as to provide a retaining force helping to hold the sensor in place. In particular, the material of the jacket may plastically deform slightly.

As well as the resilience of the jacket holding the sensor in place, over time, bone material toward the outer of the bone 132 tends to move over the shoulder portion 116 of the sensor with a further action to retain the sensor in place. Hence, during insertion, the jacket of the sensor absorbs the forces applied to the sensor thereby tending to isolate the sensor part from those forces.

In order to remove the sensor, a force is applied to the cord 104 in a direction substantially parallel to the longitudinal axis of the sensor and hole 130. If the force is applied at an angle to that direction, then the sensor tends to be retained within the bone so that the sensor tends not to be removed unless the cord is pulled on the correct direction. This helps to prevent the sensor from becoming dislodged during a medical procedure.

The properties of the metal jacket are selected so as to optimise the balance of the insertion force required, the holding or retaining force when in place and the extraction force required to remove the sensor.

In practice, the sensor can be implanted in various different bones or body parts. With regard to bones, in general, the diameter of the hole 130 into which the sensor is implanted should not be greater than approximately 10% of the diameter of the bone at the location implantation. It has been found that holes with a greater diameter are not reliable. Therefore, for a typical bone diameter of approximately 30 cm, an upper limit on the diameter of the bone hole would be approximately 3 mm and so the diameter of the sensor should similarly be approximately 3 mm or slightly greater.

As well as helping to retain sensor 100 in place in the bone, shoulders 116 also help to facilitate removal of the sensor by enabling a smooth release of the sensor through soft tissue. In practice, owing to the small diameter of the sensor, the sensor can be implanted without requiring an incision. A local anaesthetic can be used and then a guide tube, having a drill with a drill bit extending at the free end of the guide tube is used as a trocar to puncture the skin of the patient. The drill bit is then operated to drill the hole in the bone, before being withdrawn from the guide tube. The sensor is then introduced via the guide tube into the pre-drilled hole 130 and can be press fitted therein. Removal is as described above, in which a practitioner simply pulls on the cord 104, in a direction along the longitudinal axis of the hole 130 so as to release the sensor from the bone. As the central reinforcing cord 106 of the cord 104 is secured to the bar 112, on extraction, the pulling force is transmitted to the bar 112 rather than to the sensor electronics. Therefore, on removal, the forces applied to the sensor are isolated from the sensor components.

Figure 5:
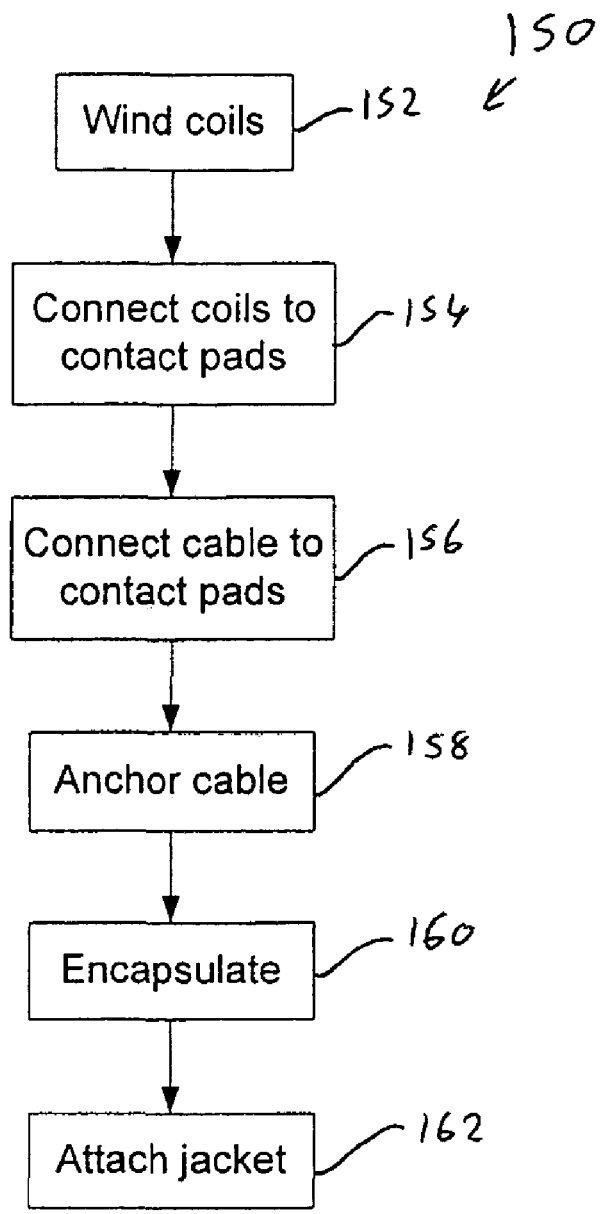
FIG. 5 shows a flow chart illustrating a method of making the sensor shown in FIGS. 1 to 4 according to the invention.

With reference to FIG. 5 there is shown a flowchart illustrating a method 150 for making the sensor shown in FIGS. 1 to 4. The method begins at step 152 at which the three mutually perpendicular coils are wound on the body or former. Then at step 154 the two free ends of each coil are each contacted to a respective contact pad by soldering. Then at step 156 the two wires of each twisted pair 108, 108', 108'', are each electrically connected to a respective wire of the induction coils by soldering so as to provide an electrical connection from the coils out of the sensor. Then at step 158, the reinforcing core 106 of the cord 104 is fastened around bar 112 for example using a knot so as to anchor the cord to the force transfer member. Then at step 160, a mould is used to encapsulate the sensor electronics and cord within an epoxy resin. After the epoxy resin has set, the encapsulated sensor part is removed from the mould and at step 162 the jacket is attached around the encapsulated sensor part and secured to the sensor by laser welding to the exposed free ends of the bar 112.

The epoxy resin both encapsulates the sensor part to prevent the ingress of moisture during use and also helps provide some structural rigidity and stability to the delicate sensor part electronics. Further, the attachment of the cord to the bar and the connection of the jacket to the bar 112 causes forces experienced by the sensor during insertion and extraction not to be passed to the sensor part components, thereby protecting the delicate sensor part electronics. Hence, the present invention provides a sensor which can easily be implanted in and extracted from a patient's bone and also protecting the delicate sensor part electronics.

What is claimed is:

1. An implantable sensor device for implanting in a body part to collect data relating to the body part, the sensor device comprising:
    a jacket having a longitudinal axis, a side wall configured to be deformed inwardly toward the longitudinal axis, and first and second ends;
    an electromagnetic sensor disposed within the jacket, and fastened to the jacket at or towards the first end of the jacket such that the sensor is at least partially isolated from compressive forces that cause the side wall of the jacket to deform inwardly.

2. The device of claim 1, wherein the jacket has at least one slit that extends generally between the first and second ends and is configured to facilitate deformation of the jacket.

3. The device of claim 2, wherein the slit extends along at least 60% of the length of the jacket.

4. The device of claim 2, wherein the jacket has at least two spaced apart slits.

5. The device of claim 2, wherein the at least one slit extends longitudinally generally aligned with the longitudinal axis.

6. The device of claim 2, wherein the jacket at its widest point has a circumference, and the ratio of the circumference to the width of the at least one slit is not more than about 10.

7. The device of claim 2, wherein the width of the at least one slit is at least about 0.1 mm.

8. The device of claim 2, wherein the width of the at least one slit is not more than about 2.0 mm.

9. The device of claim 1, further comprising a cord connected to the jacket, the cord configured to withstand a force applied via the cord to the device from the body part when the device is implanted in the body part.

10. The device of claim 9, further comprising a bar disposed within the jacket and extending between opposite side walls of the jacket, and wherein the cord is connected to the bar.

11. The device of claim 10, wherein the sensor is connected to the bar.

12. The device of claim 11, wherein the connection between the sensor and the bar is embedded in resin material.

13. The device of claim 1, wherein the jacket is tapered inwardly at least one of the first and second ends.

14. The device of claim 1, wherein the jacket comprises a first portion at the first end, a second portion at the second end, and a third portion between the first and second ends.

15. The device of claim 14, wherein the first, second and third portions of the jacket are formed from separate pieces of material.

16. The device of claim 14, wherein the cross-sectional shape of the jacket is approximately constant along the third portion of the jacket.

17. The device of claim 1, wherein the jacket comprises a single sheet of material, welded along a longitudinal seam.

18. The device of claim 1, wherein the jacket is formed from a metallic material.

19. A method of making an implantable sensor device for implanting in a body part to collect data relating to the body part, the method comprising disposing an electromagnetic sensor within a jacket and attaching the electromagnetic sensor to a first end of the jacket, the jacket having a longitudinal axis, a side wall configured to be deformed inwardly toward the longitudinal axis, the jacket further being configured to at least partially isolate the sensor from compressive forces applied to the jacket that cause the side wall of the jacket to deform inwardly.

20. A method as claimed in claim 19, further comprising the step of encapsulating the sensor in a resin before the step of attaching the jacket.

* * * * *